US012618033B2

(12) United States Patent
Nicolas et al.

(10) Patent No.: US 12,618,033 B2
(45) Date of Patent: May 5, 2026

(54) MULTI-WELL PLATE AND METHOD FOR PREPARING SAME

(71) Applicants: Centre national de la recherche scientifique, Paris (FR); Commissariat à l'énergie atomique et aux énergies alternatives, Paris (FR); UNIVERSITE GRENOBLE ALPES, Saint Martin d'Heres (FR)

(72) Inventors: Alice Nicolas, Grenoble (FR); Camille Migdal, Grenoble (FR)

(73) Assignees: CENTRE NATIONAL DE LA RECHERCHE SCIENTIFIQUE, Paris (FR); UNIVERSITE GRENOBLE ALPES, Saint Martin d'Heres (FR); COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 991 days.

(21) Appl. No.: 17/626,586

(22) PCT Filed: Jul. 9, 2020

(86) PCT No.: PCT/EP2020/069358
§ 371 (c)(1),
(2) Date: Jan. 12, 2022

(87) PCT Pub. No.: WO2021/008988
PCT Pub. Date: Jan. 21, 2021

(65) Prior Publication Data
US 2022/0235303 A1     Jul. 28, 2022

(30) Foreign Application Priority Data
Jul. 12, 2019     (FR) ...................................... 1907886

(51) Int. Cl.
C12M 1/32          (2006.01)
C12M 1/12          (2006.01)
C12N 5/095         (2010.01)

(52) U.S. Cl.
CPC ............ *C12M 23/12* (2013.01); *C12M 25/04* (2013.01); *C12N 5/0695* (2013.01)

(58) Field of Classification Search
CPC ..... C12M 23/12; C12M 25/04; C12N 5/0695; B01L 2300/0829; B01L 2300/16; B01L 2200/12; B01L 2300/12; B01L 3/5085
(Continued)

(56) References Cited

U.S. PATENT DOCUMENTS

| | | | |
|---|---|---|---|
| 6,018,388 | A | 1/2000 | Nawracala et al. |
| 9,606,108 | B2 | 3/2017 | Krishnan et al. |
| 9,758,598 | B2 | 9/2017 | Gulino et al. |
| 10,254,274 | B2 | 4/2019 | Miklas et al. |

(Continued)

FOREIGN PATENT DOCUMENTS

| | | | |
|---|---|---|---|
| FR | 3061203 | | 6/2018 |
| GB | 2334581 | * | 8/1999 |

OTHER PUBLICATIONS

International Search Report for PCT/EP2020/069358 dated Jul. 17, 2020.
(Continued)

*Primary Examiner* — Jill A Warden
*Assistant Examiner* — Jacqueline Brazin
(74) *Attorney, Agent, or Firm* — B. Aaron Schulman, Esq.; Stites & Harbison, PLLC

(57)                    ABSTRACT
The invention relates to a multi-well plate comprising a support, the upper surface of which is at least partially covered with a continuous layer of a hydrogel in contact with the lower surface of a bottomless multi-well plate, the support, the continuous layer, and the bottomless multi-well plate being adhered by means of an adhesive which extends
(Continued)

Figure 1:
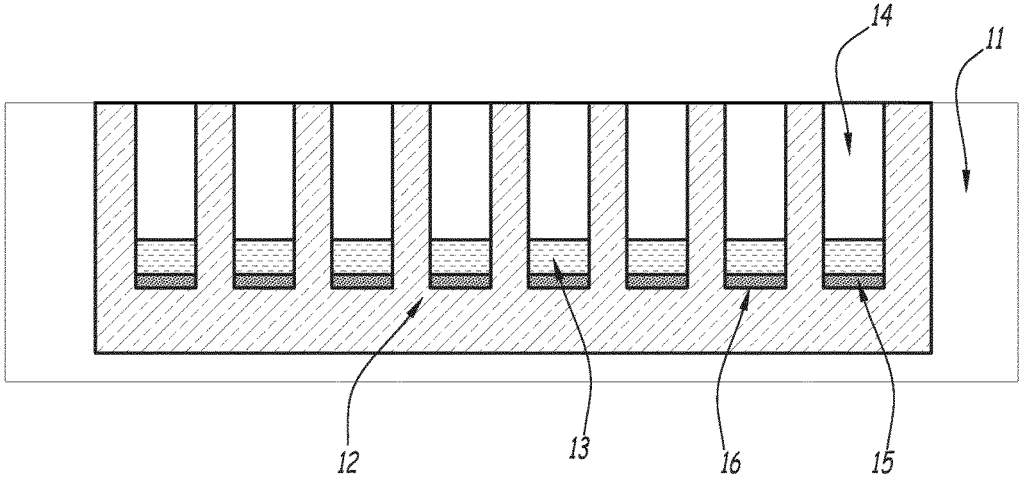

from at least certain portions of the lower surface of the bottomless multi-well plate up to certain portions of the upper surface of the support by passing through the continuous layer of hydrogel, each well of the bottomless multi-well plate being entirely surrounded by the at least certain portions of the lower surface. The application also relates to a method for preparing the multi-well plate and the use thereof for in vitro cell culture.

16 Claims, 6 Drawing Sheets

(58) Field of Classification Search
    USPC ...................................................... 435/305.2
    See application file for complete search history.

(56) References Cited

U.S. PATENT DOCUMENTS

| | | |
|---|---|---|
| 2003/0031829 A1 | 2/2003 | Tanner et al. |
| 2014/0336072 A1 | 11/2014 | Krishnan et al. |
| 2016/0002368 A1 | 1/2016 | Gulino et al. |
| 2016/0028233 A1 | 1/2016 | Cerutti et al. |
| 2018/0246411 A1 | 8/2018 | Zustiak et al. |
| 2019/0339257 A1 | 11/2019 | Miklas et al. |
| 2020/0109362 A1 | 4/2020 | Engelward et al. |

OTHER PUBLICATIONS

Preliminary Search Report for FR 1907886 dated Mar. 3, 2020.
Christal A. Worthen et al., "Mechanical Deformation Methods and Protocols" In: Methods in Molecular Biology, US, : Humana Press, vol. 1627, 24 (Aug. 24, 2017), XP055673224.

* cited by examiner 43
47
45

MULTI-WELL PLATE AND METHOD FOR PREPARING SAME

The present invention relates to a multi-well plate, the method of preparation thereof, and use thereof for cell culture or for screening of therapeutic molecules.

In many fields of biology/pharmacy it is very evident that in vitro test conditions need to correspond more closely to physiological conditions. In particular, failure to appropriately adapt to these conditions is considered largely responsible for the failure of many molecules identified in vitro to successfully be transferred to the clinical phases, due to erroneous analysis of targets and efficacy of these molecules as well as underestimation of the toxicity thereof. The cellular behaviours giving rise to these erroneous predictions are at least partially linked to the preparation of cultures in vitro under conditions that are too far removed from actual physiological conditions.

In this context, there is a need to develop multi-well plates that make it possible to perform tests under conditions that are as close as possible to physiological conditions while also retaining the advantages of such plates being used in tests, that is to say, the ease of use in implementation, reproducibility, high availability, ethics.

Products are currently being developed that offer biomimetic environments that meet these specifications: 3D environments, geometric constraints to force physiological cell geometry, microfluidic perfusion chambers to mix cell secretions and mimic co-culture, biomimetic surface chemistry for 2D culture, support with elastic base/bottom to mimic the physiological mechanical properties.

One plate production method for producing a multi-well plate for which the bottom of the wells are coated with hydrogel consists in preparing a hydrogel film on a flexible layer, then cutting the hydrogel film/flexible layer assembly in the form of pellets and inserting and assembling each pellet by means of an adhesive to the bottom of each well, as illustrated in Zustiak, S. et al. Biotechnology and Bioengineering, 2014, 111, 396-403 and in FIG. 1. The multi-well plate complies with the standard "Recommended Microplate Specifications" of the Society for Biomolecular Screening (SBS) and each well bottom may have a stiffness independent of that of other well bottoms. However, the preparation method requires a great deal of handling and manipulation. Thus the risk of contamination is very high, as is the risk of cutting residues causing degrading of the surface condition of the hydrogels. Finally, the presence of the adhesive+ flexible layer+hydrogel film stack greatly deteriorates the images obtained by inverted microscopy.

Alternatively, it is possible to prepare the hydrogel film directly at the bottom of the wells of a multi-well plate, as described in U.S. Pat. No. 8,871,499. The multi-well plate complies with the standard "Recommended Microplate Specifications" of the Society for Biomolecular Screening (SBS). Despite this however, it is likely that the gel thickness will differ from one well to another. The patent also reports that the edges of the gel in each well are softer. In addition, the monomer residues are very difficult to remove due to the narrowness of the wells, especially beyond 48 wells. However, these monomers are toxic to the cells. A product that neutralises free radicals is added, but comes with the risk of partially retaining the toxicity linked to the mutagenic, carcinogenic and reprotoxic properties of bis-acrylamide. Moreover, even if it is possible to vary the stiffness of the hydrogel between the wells by varying the monomer composition of the solution used, the preparation of soft hydrogels is difficult in practice due to the rapidness in reaching the limit at which the crosslinking is no longer covalent but entangled ("entanglement"), and the gel then exhibits strong spatial heterogeneities in stiffness. Finally, this method of preparation precludes creating controlled stiffness gradients within a well.

Figure 2:
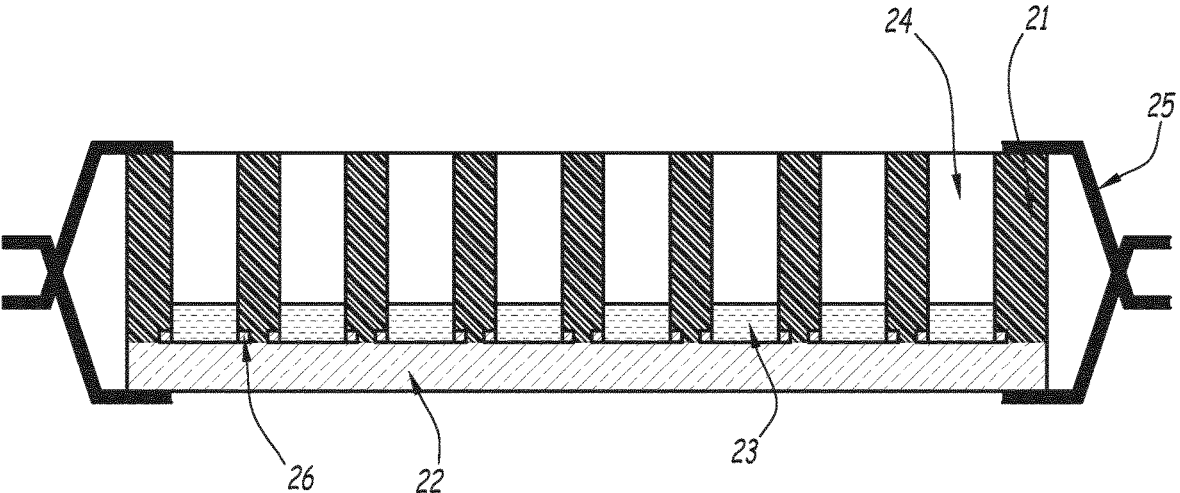

Ahmed, N.; et al. Tissue engineering. Part C, Methods, 2016, 22, 543-551 describe the preparation of a multi-well plate comprising of the preparation by photopolymerisation through a photomask of a hydrogel in the form of pellets, followed by the assembly of these hydrogel pellets with a support consisting of wells drilled in a piece of plastic. The assembly is held in place by clamps, and annular seals located at the base of each well ensuring the sealing of each well. FIG. 2 illustrates such a plate. The resulting multi-well plate obtained is not compatible with robots and microscope incubators and does not comply with the standard "Recommended Microplate Specifications" of the Society for Biomolecular Screening (SBS), which greatly limits its use. In addition, it is necessary to position as many seals as there are wells on the plate, which makes the method very unsuitable for plates comprising a large number of wells.

The patent application WO 2013/074972 describes a platform for biological assays including a substrate in the form of a support (110), at least one surface of which is coated with position markers (112), a first deformable layer (120) on top of the base substrate, and a second deformable layer (130) positioned on top of the first deformable layer, this second deformable layer being embedded with deformation markers (132). A bottomless multi-well layer (150) can be positioned on top of the second deformable layer, possibly by means of adhesive proteins. This patent application teaches that hydrogels, such as polyacrylamide, may be used as materials for forming the deformable layers, but have numerous drawbacks. Polydimethylsiloxane (PDMS) would be more suitable. In addition, this application does not describe any adhesive, and a fortiori no adhesive that extends from the bottomless multi-well layer to the first deformable layer by passing through the second deformable layer.

The patent application WO 2017/223254 describes a multi-well plate prepared from agarose or another type of hydrogel. A bottomless 96-well plate is then compressed on top of the multi-well plate in order to create macro-wells. This application is also silent on the use of an adhesive.

The patent application WO 2015/061907 describes a bioreactor in the form of a multi-well plate for cell culture, each well comprising a chamber configured so as to carry out 3D tissue culture, with at least one deformable support element affixed to each chamber and preferably being polymeric. In one embodiment, the bioreactor includes a polymethyl methacrylate (PMMA) substrate, polymer films (for example, poly(octamethylene maleate [anhydride] citrate) or POMac) as a deformable element, a bottomless 96-well plate, and a covering ("cap") for the plate. Double-sided adhesives may be adhered to the bottomless plate. However, as explained below, the inventors have demonstrated that such an adhesive does not serve to ensure sufficient sealing for the wells when the polymer film is a hydrogel.

According to a first object, the invention relates to a multi-well plate comprising a support, the upper surface of which is at least partially covered with a continuous layer of a hydrogel which has a stiffness of from 0.05 to 100 kPa, as measured by atomic force microscopy, and is in contact with the lower surface of a bottomless multi-well plate, the said support, the said continuous layer, and the said bottomless multi-well plate being adhered by means of an adhesive which extends from at least certain portions of the lower surface of the bottomless multi-well plate up to certain portions of the upper surface of the support by passing through the continuous layer, the bottom of each well of the multi-well plate being entirely surrounded by the said at least certain portions of the lower surface of the bottomless multi-well plate. Within the meaning of the application, a hydrogel comprises a polymer matrix and an aqueous phase within the polymer matrix, the polymer matrix forming a three-dimensional network that is capable of swelling in the presence of the said aqueous phase. The solubility of the polymer matrix at 1 bar and 25° C. in this aqueous phase is generally less than 1 g/L. The aqueous phase may be water.

The polymer of the polymer matrix of the hydrogel may be homopolymeric (three-dimensional network formed from a homopolymer), copolymeric (three-dimensional network formed from a copolymer) or multipolymeric (three-dimensional network of "interpenetrating polymeric gel" (IPN)).

Generally, the polymer matrix comprises (or indeed is constituted of) a polymer selected from among:

polyacrylamides;

polyethylene glycols, polypropylene glycols and ethylene glycol or propylene glycol copolymers, these latter optionally comprising units resulting from the polymerisation of (meth)acrylate compounds;

polysaccharides, optionally comprising repeating units resulting from the polymerisation of (meth)acrylate compounds;

(co)polymers resulting from the polymerisation of diacrylate and/or (meth)acrylate compounds;

polyvinyl alcohols comprising repeating units resulting from the polymerisation of (meth)acrylate compounds;

dextrans comprising repeating units resulting from the polymerisation of (meth)acrylate compounds;

polypropylene fumarates and poly(propylene fumarate-co-ethylene glycol); and the combinations thereof.

Polymer matrices based on polyacrylamides, and in particular resulting from the polymerisation of acrylamide and N,N-methylenebisacrylamide, are particularly preferred.

The term "(meth)acrylate compounds" is understood to refer to compounds derived from acrylate or methacrylate, for example selected from among acrylic acid (AA), methacrylic acid (MA), ethylene glycol dimethacrylate (EGDMA), 2-hydroxyethyl methacrylate (HEMA), sulfopropyl acrylate, where the acids may be in the form of a salt, in particular sodium or potassium.

Figure 3:
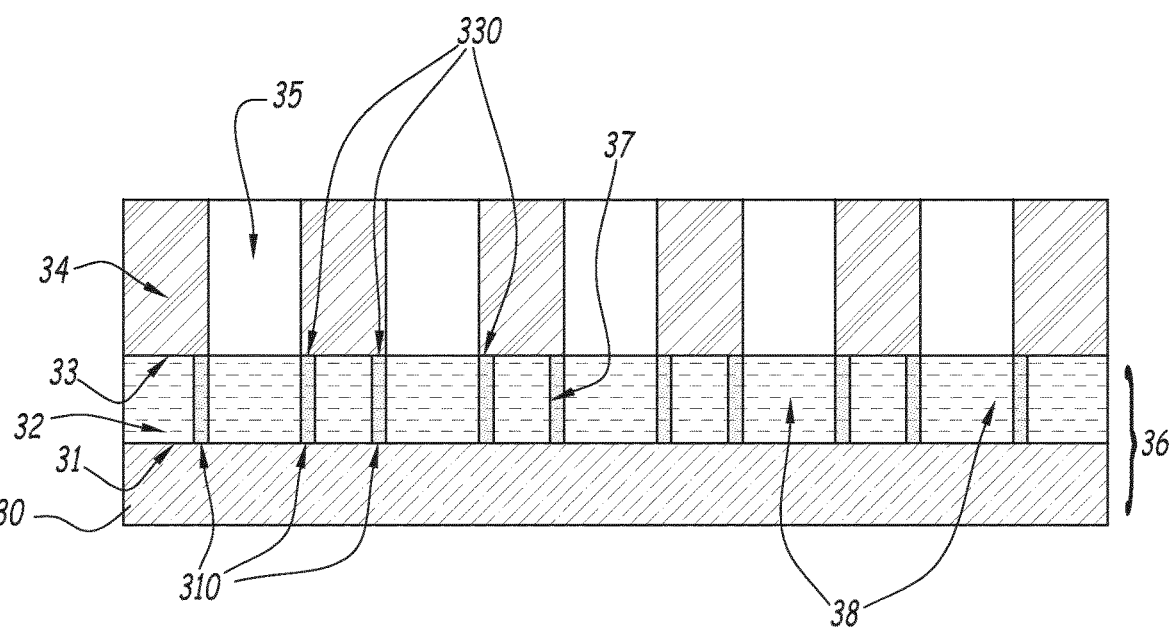

The term "layer of a hydrogel" is understood to indicate that the layer comprises, or indeed is constituted of a hydrogel. This layer is continuous. The hydrogel forms the bottom of the wells, and also extends between the wells (FIG. 3).

The continuous layer of a hydrogel in dehydrated form generally has a thickness ranging from 0.1 to 1 mm, typically from 0.1 to 200 µm, preferably from 0.1 to 120 µm, in particular from 10 to 120 µm, for example from 20 to 50 µm. The thickness of a hydrogel in dehydrated form is independent of its stiffness, and is therefore easier to determine than that of a partially or fully hydrated hydrogel, since the thickness thus then depends on the stiffness of the hydrogel.

The stiffness of the hydrogel is from 0.05 to 100 kPa, preferably from 0.1 kPa to 50 kPa.

The local stiffness and therefore the variability of stiffness can be determined by atomic force microscopy (AFM), for example by following the protocol described on pages 29 and 30 of the patent application WO 2013/079231.

Within the same given well, the stiffness of the hydrogel may be identical or variable.

In one embodiment, within the same given well of the multi-well plate, the variability in the stiffness of the hydrogel at the micrometer scale is less than 10%, preferably less than 5%. In other words, the difference in stiffness between two points of the hydrogel separated by 1 µm does not exceed 10%, preferably 5%. The stiffness of the hydrogel is thus then identical within the same well.

In another embodiment, within the same given well, the hydrogel comprises at least two contiguous zones of distinct stiffness exhibiting a stiffness gradient greater than or equal to 0.05 kPa/µm. The stiffness of the hydrogel is thus then variable within the same well. The hydrogel within a single well may exhibit distinct stiffness patterns.

The stiffness of the hydrogel may be identical or variable from one well to another.

In one embodiment, the variability in the stiffness of the hydrogel between two wells, preferably between all the wells, is less than 10%, preferably less than 5%. The stiffness is thus then identical between the two wells (or among all the wells).

In another embodiment, the variability in the stiffness of the hydrogel between at least two wells is greater than 20%, preferably greater than 30%. The stiffness is thus then variable between these two wells.

The stiffness within the same well and between the wells is independent. For example:

the hydrogel exhibits uniform stiffness: all well bottoms have identical stiffness (that is to say the variability in the stiffness of the hydrogel at the micrometer scale is less than 10%, preferably less than 5%);

the stiffness of the hydrogel is identical within the same well, but the stiffness varies from one well to another;

the stiffness of the hydrogel is variable within the same well, and the stiffness varies from one well to another.

Thus, advantageously, the stiffness and the mechanical properties of the hydrogel within the same given well and between the wells may be adapted according to the desired use.

The surface of the hydrogel of at least one of the wells, preferably of each well, may be functionalised with a polysaccharide and/or a protein and/or a peptide, in particular with a protein and/or a peptide inducing cell adhesion via integrins, it being possible for such a protein to be fibronectin, fibrinogen, collagen, laminin, vitronectin or peptides such as RGD peptides.

Within the meaning of the application, the term "lower surface of the bottomless multi-well plate" is understood to refer to the surface of the multi-well plate which is facing or which is intended to be facing the continuous layer of a hydrogel. Under normal conditions of use of the multi-well plate according to the invention, the multi-well plate according to the invention, and therefore the bottomless multi-well plate that it comprises, are horizontal, and the lower surface of the bottomless multi-well plate is the lower-most surface of the bottomless multi-well plate.

Within the meaning of the application, the term "upper surface of the support" is understood to refer to the surface of the support which is covered or which is intended to be covered with the continuous layer of a hydrogel. Under normal conditions of use of the multi-well plate according to the invention, the multi-well plate according to the invention, and therefore the support it comprises, are horizontal, and the upper surface of the support is the upper-most surface of the support.

Generally the support is made of glass or plastic.

Preferably, the hydrogel of the continuous layer is covalently bonded to the support.

The term "multi-well plate" is understood to refer to a plate comprising of at least two wells, typically 6, 48, 96, 384 or 1024 wells.

The bottomless multi-well plates are plates comprising at least two hollow cylinders which have their axes parallel to each other. These cylinders form the wells. The plates are generally made of polymer, for example polystyrene. The bottomless multi-well plates are commercially available. For example mention may be made of the 'Greiner Bio One 96 wells No Bottom' plates.

The support, the continuous layer made of hydrogel, and the bottomless multi-well plate are adhered by means of an adhesive which extends from at least certain portions of the lower surface of the bottomless multi-well plate to the upper surface of the support by passing through the continuous layer made of hydrogel. The bottom of each well of the multi-well plate is entirely surrounded by at least certain portions of the lower surface of the bottomless multi-well plate. The continuous layer of hydrogel is thus is partitioned into compartments by means of the adhesive. The adhesive serves as the means to ensure the tight sealing of the wells, that is to say providing a sealing that endures for at least one month. This tight sealing is generally observable with the naked eye. It is also possible to test it by introducing a solution comprising a dye into one of the wells and checking to ascertain no migration of the latter to the adjacent wells.

Generally, for each zone of the continuous layer that is situated under a well of the bottomless plate, less than 50% by volume, in particular less than 25% by volume, preferably less than 10% by volume, typically less than 5% by volume, ideally 0% by volume thereof is occupied by the adhesive. The top portion of one of these zones constitutes the bottom of a well. It is preferred for as little as possible of the adhesive to be present in the hydrogel situated at the bottom of each well so as not to alter the stiffness of the hydrogel that forms the bottom of the well. The volume of each zone can easily be calculated based on the radius of the wells and the thickness of the continuous layer. In order to determine the volume occupied by the adhesive in these zones, it is possible to effect several sections of each zone and compile the results. More simply, a visual observation of each well serves to enable observing the extent to which the adhesive spreads in each well.

The adhesive is preferably biocompatible and non-toxic. Cyanolite-based adhesives are generally avoided because of their toxicity. The adhesive is preferably resistant to all the chemical products used during the analyses (paraformaldehyde, methanol for example). Typically, this is an adhesive intended for use in medical devices. Examples of adhesives that may be used are silicone adhesives (for example the adhesive Loctite SI5398) or adhesives derived from mercapto esters (for example Norland Optical Adhesive NOA68 or NOA81). It may be an adhesive obtained by crosslinking, for example with ultraviolet rays, or by solvent evaporation.

Advantageously, the multi-well plate complies with the standard "Recommended Microplate Specifications" of the Society for Biomolecular Screening SBS, which serves to ensure compatibility with robots and microscope incubators. In particular, the physical characteristics of multi-well plates are conducive to ease of use in high magnification microscopy.

Preferably, the multi-well plate according to the invention is capable of being prepared by the method described below.

According to a second object, the invention relates to a plate preparation method for preparing a multi-well plate that comprises the steps consisting in:

a) providing a substrate comprising a continuous layer of a hydrogel which has a stiffness of from 0.05 to 100 kPa, as measured by atomic force microscopy, the said layer at least partially covering the upper surface of a support;

b) applying a liquid adhesive at 20° C. over at least certain portions of the lower surface of a bottomless multi-well plate, the bottom of each well being entirely surrounded by the at least certain portions of the lower surface of the bottomless multi-well plate, c) assembling the substrate and the bottomless multi-well plate by bringing into contact the surface of the hydrogel of the substrate with the lower surface of the bottomless multi-well plate that is at least partially covered with liquid adhesive, whereby the liquid adhesive at least partially penetrates within the continuous layer of a hydrogel.

The method may comprise, prior to the step a), a step a) of substrate preparation for preparing the substrate by polymerisation of a mixture of monomers that are capable of forming the polymer matrix of the hydrogel, the polymerisation being carried out on the support, which thus results in obtaining the support that is at least partially covered with a continuous layer of hydrogel. The polymerisation may be a photopolymerisation or chemical polymerisation process.

In order to control the thickness of the hydrogel layer, the polymerisation may be carried out between the support and a slide acting as a cover, which are spaced apart from each other by a distance equal to the desired thickness, that is to say preferably from 0.1 to 120 μm, in particular from 40 to 120 μm, for example by means of spacers.

In step b), the liquid adhesive is applied over at least certain portions of the lower surface of a bottomless multi-well plate in a manner such that the bottom of each well is entirely surrounded by the at least certain portions of the lower surface of the bottomless multi-well plate. The liquid adhesive applied therefore entirely surrounds the bottom of each well, which will serve to ensure the tight sealing of each well during subsequent uses of the multi-well plate. The term "bottom of the well of the bottomless multi-well plate" is understood to refer to the end of the well on the lower surface side of the bottomless multi-well plate.

The shape(s) of at least certain portions of the lower surface of the bottomless multi-well plate over which the adhesive is applied can be quite diverse.

Figure 4:
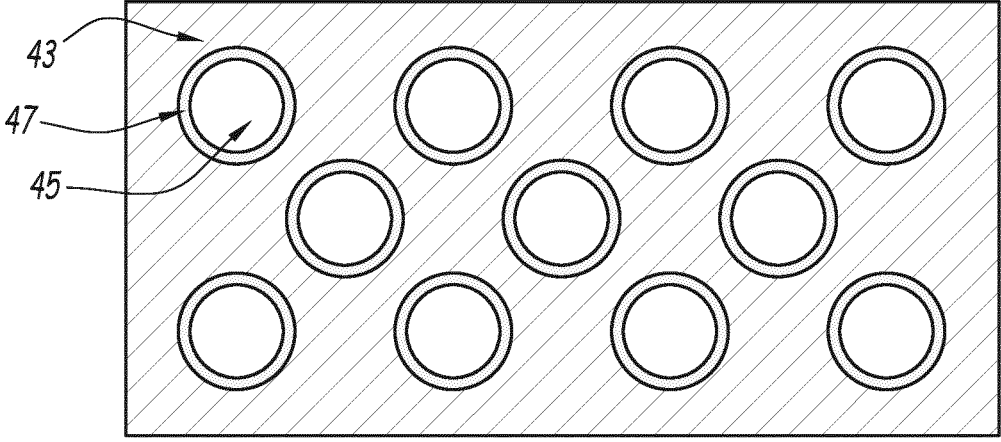

In a first embodiment, the liquid adhesive is applied on to the lower surface of the bottomless multi-well plate in the form of circles, the bottom of each well being entirely surrounded by a circle (FIG. 4). The wells of the bottomless multi-well plate are cylindrical, and the bottom of each well forms a circle. Each circle of liquid adhesive entirely surrounding the bottom of a well may or may not touch the circle formed by the bottom of the well.

Figure 5:
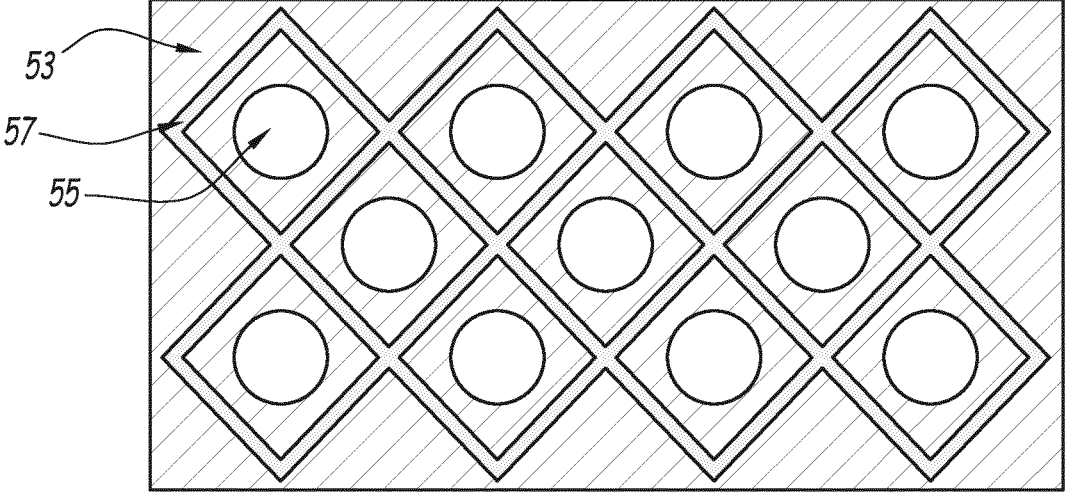

In a second embodiment, the liquid adhesive is applied on to the lower surface of the bottomless multi-well plate in the form of a grid, each well bottom being entirely surrounded by a tile of the grid (FIG. 5). A tile of the grid may be square-, rectangle-, or diamond-shaped depending on the arrangement of the wells relative to each other in the bottomless multi-well plate.

These two embodiments are advantageous in that they make it possible to minimise the amount of adhesive to be used.

Figure 6:
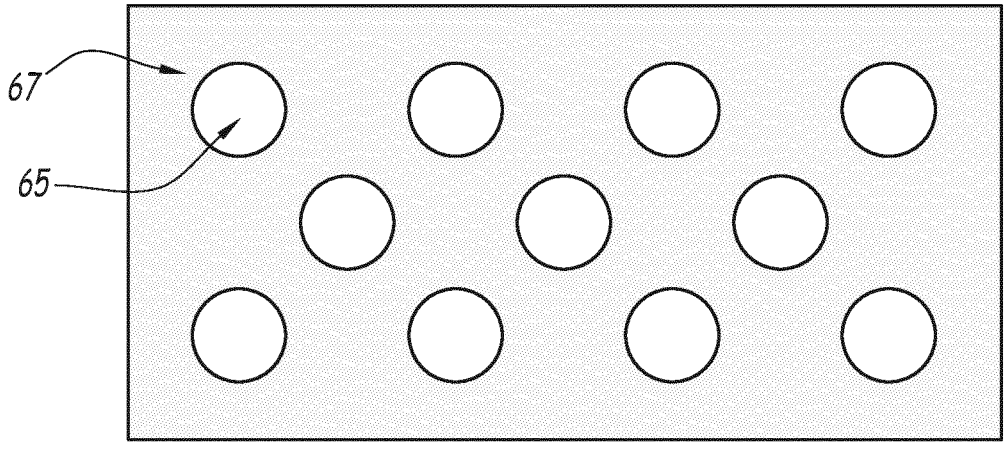

In a third embodiment, the liquid adhesive is applied on to the entirety of the lower surface of the bottomless multi-well plate (FIG. 6). This embodiment is easy to implement, for example by passing a roller over the lower surface, or else by bringing into contact the entirety of the lower surface with a string of adhesive, however it is the embodiment that requires the most liquid adhesive.

In the method, the liquid adhesive is applied on to at least certain portions of the lower surface of a bottomless multi-well plate. Alternatively, it would be possible to apply the liquid adhesive on to at least certain portions of the surface of the continuous layer of hydrogel. However, it would then be necessary to put as little adhesive as possible on the surface of the continuous layer that would coincide with the site of the wells. It is simpler to apply the liquid adhesive to the lower surface of the bottomless multi-well plate in order to minimise the amount of adhesive at each well. Preferably, after the step c) of assembly, for each zone of the continuous layer that is situated under a well of the bottomless plate, less than 50% by volume, in particular less than 25% by volume, preferably less than 10% by volume, typically less than 5% by volume thereof is occupied by the liquid adhesive.

The method may comprise, prior to the step c), a step c0) of partial dehydration of the hydrogel, for example by heating the substrate between 30 and 50° C., typically for a period of 1 hour to 6 hours. This dehydration allows the surface of the hydrogel to adhere better to the lower surface of the bottomless multi-well plate that is at least partially covered with adhesive during step c).

During step c), the substrate and the bottomless multi-well plate are assembled by bringing into contact the surface of the hydrogel of the substrate with the lower surface of the bottomless multi-well plate that is at least partially covered with liquid adhesive, whereby the liquid adhesive at least partially penetrates within the continuous layer of a hydrogel.

The adhesive used in step b) is a liquid adhesive applied at 20° C., which allows it to at least partially penetrate into the hydrogel during step c).

There existed a technical bias relating to the use of liquid adhesive to prepare a multi-well plate. A person skilled in the art specialising in hydrogels generally would avoid using a liquid adhesive due to the fear of this causing deterioration of the physicochemical properties of the hydrogel. There was a technical difficulty in adhering a hydrogel in a manner such as to ensure the strength of the multi-well plate obtained by preventing partial or total detachment of the bottomless multi-well plate and/or of the support in the event of shocks occurring during normal human and robotic handling (in particular during dehydration/rehydration of the hydrogel) and above all ensuring effective tight inter-well sealing. In addition, a person skilled in the art specialising in multi-well plates, whereof the main applications are in biology, also avoids using an adhesive, due to the fear of the latter being toxic for the biological materials which will be introduced into the well. However, the present inventors have demonstrated that it is possible to use a liquid adhesive to prepare the multi-well plate without denaturing the hydrogel at the bottom of the wells (except for generating some edge effects at the periphery of the wells; however these edge effects exist for all multi-well plates, regardless of the method of preparation thereof).

This penetration of the adhesive within the continuous layer may be partial: that is to say that the adhesive does not penetrate across the entire thickness of the continuous layer made of hydrogel; or total: that is to say, that it passes through the continuous layer made of hydrogel until it reaches certain portions of the upper surface of the support (generally the portions of the upper surface of the support situated vertically directly under the portions of the lower surface of the bottomless multi-well plate over which the adhesive was applied). Total penetration may require increasing the quantity of liquid adhesive applied during the step b) as compared to partial penetration. When it is total, the method then makes it possible to prepare the multi-well plate according to the first object of the application and the tight sealing of the wells of the plate is effectively enhanced as compared to partial penetration. During total penetration of the adhesive, the tight sealing of the wells is indeed maintained even if the hydrogel undergoes a dehydration step after the step c). This being the case, the quantity of adhesive, and therefore the cost of the plate, can advantageously be minimised when the penetration of the liquid adhesive is partial. When the multi-well plate is used shortly after its preparation and/or when the conditions of use are mild (notably when they do not induce dehydration of the hydrogel), a partial penetration of the adhesive is sufficient to ensure tight sealing for at least 12 hours.

Generally, the liquid adhesive has a viscosity of from 0.1 to 50 Pa·s (100 to 50,000 cPs) at 25° C. as measured according to the standard NF EN 12092 of August 2002. Preferably, the adhesive selected is an adhesive capable of adhering to both the material of the support (generally made of glass or plastic) and the material of the bottomless plate (generally made of polymer, often polystyrene). An adhesive as defined above can in particular be used. Preferably, an adhesive is selected in which the monomer (or the monomers, in the event of multiple monomers) is capable of passing through the pores of the hydrogel of the continuous layer. The size of the pores is variable from one hydrogel to another. This ability to pass through the pores may for example be measured by means of particle exclusion microscopy (PEM) by adding a solution comprising of particles of known and monodisperse size as explained in paragraph 2.2 of Uruena et al., Biotribology, 1-2, 2015, 24-29.

The method may include, after the step c), a step d) of adhesive activation for activating the adhesive, generally by crosslinking, for example by ultraviolet illumination when the adhesive comprises a photopolymerisable polymer. When required, the activation of the adhesive, should be sufficient. It generally suffices to follow the recommendations of the supplier of the liquid adhesive.

The method may include, after the step c), a step d') of drying of the adhesive, in particular to evaporate the solvent where one is contained therein.

The method may include, between the steps a) and c), a step a1) of application of a polysaccharide and/or a protein and/or a peptide on to at least a portion of the surface of the hydrogel of the substrate. Alternatively, the method may include, after the step c) (or after the optional step d) or d')), a step e) of application of a polysaccharide and/or a protein and/or a peptide on to the surface of the hydrogel of at least one well, preferably of each well. This step a1) or e) will provide the means to obtain, at the conclusion of the method, a plate for which the surface of the hydrogel of at least one of the wells is functionalised with a polysaccharide and/or a protein and/or a peptide, in particular with a polysaccharide, a protein and/or a peptide able to induce cell adhesion via integrins. The proteins and/or the peptides and/or the polysaccharides made use of in the step a1) or the step e) may have been modified in order for them to bear a functional group capable of reacting with the polymer matrix of the hydrogel. The step a1) or the step e) may be followed by a step i) of covalent grafting of the polysaccharide and/or of the protein and/or of the peptide onto the hydrogel, which thereby makes it possible to immobilise the same definitively and to prevent the peptide and/or protein from being eliminated during rinsing, for example.

The preferred embodiments described here above for the multi-well plate are quite certainly applicable to the preparation method for preparing a plate.

The method according to the invention is easy to implement. It does not require complex equipment. It is inexpensive, and easily reproducible. The method makes it possible to design a 6 well plate or a 384 well plate with equal ease and with similar conditions.

According to a third object, the invention relates to a multi-well plate that it is possible to obtain by the method described here above.

According to a fourth object, the invention relates to the use of the multi-well plate described here above for in vitro cell culture, in particular for the culturing and differentiation of stem cells or for the screening of therapeutic molecules.

Preferably, the stem cells are not human embryonic stem cells.

The invention also relates to a cell culture method in which the multi-well plate described here above is seeded with cells, and the cells are then cultured.

The invention also relates to a screening method for screening of therapeutic molecules, which includes: the deposition in the wells of the afore-described multi-well plate of a ligand; the bringing into contact of the molecules to be tested with the said ligand; followed thereafter by the identification of the molecules to be tested which have bound themselves to the said ligand. The ligand may be a receptor, a nucleic acid, a peptide or a protein.

The examples and figures below illustrate the invention.

FIGURES

FIG. 1: Diagram of a cross sectional view of a multi-well plate according to Zustiak (comparative). The cutouts in the form of pellets of a hydrogel film 13/flexible layer 15 assembly are assembled with the adhesive 16 at the bottom of each well 14 of a support 12 of a multi-well plate 11 with standardised dimensions.

FIG. 2: Diagram of a cross sectional view of a multi-well plate according to Ahmed (comparative). The hydrogel pellets 23 are assembled with a support consisting on the one hand of a piece of plastic 21 with wells 24 drilled, and on the other hand, a plate 22 made of glass or plastic that is covered with a plastic film. The plastic piece 21/plate 22 assembly is held together by clamps 25. Annular seals 26 situated at the base of each well 24 ensure the tight sealing of each well 24.

FIG. 3: Diagram of a cross sectional view of a multi-well plate according to the invention. A substrate 36 comprises a support 30, of which the upper surface 31 is covered with a continuous layer 32 of a hydrogel in contact with the lower surface 33 of a bottomless multi-well plate 34. Five wells 35 of the bottomless multi-well plate 34 are visible. The support 30, the continuous layer 32, and the bottomless multi-well plate 34 are adhered by means of an adhesive 37 which extends from certain portions 330 of the lower surface 33 of the bottomless multi-well plate 34 up to certain portions 310 of the upper surface 31 of the support 30 by passing through the continuous layer 32. The zones 38 of the continuous hydrogel layer are situated under the wells of the bottomless plate. FIG. 3 shows an ideal case where these zones are free of adhesive and where there is no adhesive at the bottom of the wells (for each zone of the continuous layer situated under a well of the bottomless plate, 0% by volume thereof is occupied by the adhesive).

FIG. 4: Diagram of a bottom view of the bottomless multi-well plate obtained at the end of the step b) when the liquid adhesive 47 has been applied in the form of circles on to the lower surface 43 of the multi-plate bottomless well, the bottom of each well 45 being surrounded by a circle of liquid adhesive. In this figure, the circle of liquid adhesive touches the circle formed by the bottom of the well.

FIG. 5: Diagram of a bottom view of the bottomless multi-well plate obtained at the end of the step b) when the liquid adhesive 57 has been applied in the form of a grid on the lower surface 53 of the multi-plate bottomless well, the bottom of each well 55 being entirely surrounded by a tile of the grid.

FIG. 6: Diagram of a bottom view of the bottomless multi-well plate obtained at the end of the step b) when the liquid adhesive 67 has been applied over the entirety of the lower surface of the bottomless multi-well plate (which is therefore completely covered with liquid adhesive 67 and is no longer visible, unless the adhesive is transparent).

EXAMPLES

Example 1: Preparation of a 96-Well Plate with a Bottom Having Stiffness of 25 kPa The hydrogel consists of a layer of polyacrylamide, with a thickness of approximately 60 µm. It was prepared according to the method described in the patent application WO 2013/079231. Its preparation consists in the crosslinking of a photosensitive solution of monomers between a base glass slide, which serves as a support for the hydrogel, and a mask, which ensures the flatness of the free surface and eventually makes it possible to print the modulations of stiffness in the event of the UV transmission rate thereof being modulated.
Preparation of the Base Coverslip A glass coverslip having dimensions of 75×113 mm^2 is cleaned in a solution of 0.1 mol/L of sodium hydroxide for 10 min. It is thereafter rinsed thoroughly with water, then with ethanol, and air dried. 3000 µl of a silane solution comprising 56 µl of Bind-Silane (GE Healthcare), 485 µl of 10% acetic acid, and 14.46 ml of ultra-pure ethanol are deposited on the coverslip and rubbed with a polyester knit fabric wiper until all traces of solution disappear. A glass coverslip is thus obtained that has aldehyde functional groups at its surface, which will enable the covalent grafting of the polyacrylamide gel.
Preparation of the Mask A transparent mask made of glass that makes it possible for the surface of the hydrogel to be rendered planar is treated with a fluorinated silane so as to limit the adhesion thereof to the hydrogel: the mask (100×110 mm$^2$) is washed in a solution of oxygenated water/concentrated sulfuric acid in proportions of 1:2, for 10 minutes. Thereafter its surface is rendered hydrophobic by an Optool treatment (Daikin DSX): immersion for 1 minute in an Optool solution diluted to 1/1000 in perfluorohexane, then for 1 hour in water vapour at 80° C., then immersion under slow agitation for 10 minutes in perfluorohexane.
Preparation of the Hydrogel (Step a) of the Method)
Composition:
  10% acrylamide (250 µl of solution initially at 40%)
  0.5% N,N'-methylenebisacrylamide (Bis) (250 µl of solution initially at 2%)
  0.2% Irgacure 819 w/v (Ciba, photo-initiator)
  1% propylamine (initiator)
  deionised water (490 µl)

Irgacure 819 is weighed in a flask that is opaque to UV light. Propylamine is added to the latter, the entirety of which is then heated at 50° C. for 2 minutes. After heating, a homogeneous, transparent solution is obtained. Water, acrylamide, and bis acrylamide are added quickly therein. Using a pipette, the entire mixture is gently homogenised in order to limit the incorporation of oxygen.

400 μL are deposited on the glass coverslip pretreated according to the above protocol. The coverslip is placed on a sample holder having spacers which maintain a spacing of 40 μm between the coverslip and the transparent mask, deposited on the spacers. The whole unit (mask, solution, coverslip) is illuminated by using a UV insolator (UVKub Kloé 1) (40 mW/cm² at 365 nm) for 15 s. This unit is then immersed in deionised water in order to detach the mask from the hydrogel using forceps. The hydrogel is rinsed 3 times with deionised water and conserved in deionised water.

Characterisation

The local stiffness of the gel is measured using an atomic force microscope (AFM) in aqueous medium (JPK brand). The resistance of the gel to the insertion of the tip is recorded. Thirty-eight 100 μm×100 μm regions distributed randomly over the surface of the hydrogel are scanned. The scans are carried out with a step of 10 μm. This results in a series of indentation curves. Each curve is processed according to the manufacturers protocol with an elastic indentation model. This results in a Young's modulus of 25.7±1.7 kPa.

Assembly of the 96-Well Plate

The hydrogel is dehydrated on a hot plate at 37° C. for 1 hour.

An adhesive film (Norland Adhesive 68) is deposited on the lower surface of a 96-well no bottom plate (Greiner Bio One 96 wells No Bottom), in a manner such that the adhesive completely surrounds each well (step b) of the method). The hydrogel is gently deposited on the adhered surface of the 96-well plate (step c) of the method). The adhesive is allowed to spread for 1 minute. The whole assembly is fixed by UV illumination (5 min, UV lamp: Kloé UVKub 1, 40 mW/cm²) (step d) of the method).

Surface Functionalisation (Step e) of the Method)

In order to enable cell culture, the surface of the hydrogel is functionalised with a cell adhesion protein, in this case fibronectin.

The fibronectin protein is previously coupled to the hetero-bifunctional crosslinker Sulfo-NHS-LC-Diazirine (sulfosuccinimidyl-6-(4,4'-azipentanamido)hexanoate, from ThermoScientific Pierce; trade name: sulfo-LC-SDA, with a molar ratio of 1/480.

1 mg of fibronectin (Roche) is dissolved in 400 μL of ultrapure deionised water at 37° C. for 30 min. 0.3 mg of sulfo-LC-SDA, weighed in the dark, is dissolved in the fibronectin solution for 30 min at ambient temperature. This operation is repeated a second time with 0.2 mg of sulfo-LC-SDA, thereby resulting in a molar ratio of 1/480. This protocol makes it possible to react the sulfo-NHS functional group of the sulfo-LC-SDA with the amine groups of the fibronectin while limiting the hydrolysis of the sulfo-LC-SDA.

The compound formed is a fibronectin molecule coupled to a photoreactive (photosensitive) diazirine functional group.

The compound formed is dialyzed in a dark room through a 6-8000 membrane and at 4° C. against 2 L of phosphate-buffered saline 1×PBS+/+ for 48 hours with the PBS changed after 24 hours. It is then aliquoted into small volumes (25 and 50 μL) and stored frozen at −20° C.

In a room with UV-free lighting, 8 mL of fibronectin solution conjugated according to the above protocol is prepared at a concentration of 8.1 μg/mL in sterile deionised water. 50 μL of this solution are deposited using a pipette in each well of the assembly. The assembly is placed on a hot plate at 37° C. under a laminar flow hood until complete evaporation of the fibronectin solution from the surface of the hydrogel. The whole assembly is then illuminated with the UVKub Kloé 1 lamp for 5 min. Each well is then gently rinsed 3 times with a solution of PBS+/+. Thereafter the functionalised assembly is stored hydrated in a solution of PBS+/+, at 4° C., in the dark.

Cell Culture

The human glioblastoma cell line LN229 is inoculated at a rate of 10,000 cells per well in a volume of 100 μl of Dulbecco's Modified Eagle Medium (DMEM) (Gibco) supplemented with 10% fetal calf serum (PAA) and 1% of a mixture of antibiotic and antimycotic solution (ATAM, Thermo Fisher Scientific). After culturing for 24 hours, the culture medium is removed by inverting the assembly, and is replaced with a fixing solution (1×PBS+/+ containing 4% paraformaldehyde) for 45 min.

Characterisation of Cells

The condition of the cells is characterised by immuno-fluorescence after 24 hours of culturing. The labelling of tubulin, vinculin and nuclei is carried out as follows:

The LN229 cells in each well are incubated for 15 min in 100 μl of a permeabilisation solution (1×PBS+/+ containing 0.5% of Triton X100), then the solution is removed by inverting the assembly, followed by addition of 100 μl of saturation buffer consisting of a solution of 1×PBS+/+—0.1% Tween20—2% Bovine Serum Albumin (BSA), to each well for a period of 30 min with slow agitation at ambient temperature. The saturation solution is removed and replaced with 50 μL (in each well) of a solution of 1×PBS+/+—0.1% Tween20—2% Bovine Serum Albumin (BSA) containing the primary monoclonal anti-total tubulin antibodies (produced in mice—YL1/2, Abcam—and diluted to 1/4000) and the primary monoclonal anti-vinculin antibodies (produced in rats—clone 7F9, Santa Cruz—and diluted to 1/1000).

The antibodies are left for 1 hour under slow agitation at ambient temperature. The primary antibody solution is then removed by inversion and the cells in each well are rinsed 3 times with 150 μL of a solution of 1×PBS+/+—0.1% Tween20—2% Bovine Serum Albumin (BSA). The primary antibodies are then revealed with 50 μL per well of a solution of 1× PBS+/+—0.1% Tween20—2% Bovine Serum Albumin (BSA) containing the anti-mouse secondary antibodies coupled to Alexa 488, and anti-rat secondary antibodies coupled to Cyanine 3 (respectively from LifeTechnologies and Rockland), for 1 hour under slow agitation at ambient temperature and in the dark. The secondary antibody solution is removed and the cells in each well are rinsed 3 times with 150 μL of a solution of 1×PBS+/+—Tween20 0.1%—2% BSA. Then, for 5 min, a solution of 1×PBS+/+ containing Hoechst diluted to 1/1000 is added in the amount of 100 μl/well. After removal of this solution by inversion, the fixed and labelled cells are stored in a solution of 1×PBS+/+ at 4° C. and in the dark.

The acquisition at 20× and the analysis of the images (9 images per well) are carried out in an automated manner (HCS/HCA High Content Screening/High Content Analysis) by an ArrayScan VTI (Thermo Fisher Scientific). The results demonstrate that the cell culture was effective in each well.

Example 2: Sealing of Wells Depending on the Use of a Liquid/Non-Liquid Adhesive Polyacrylamide hydrogels fixed on 30 mm glass coverslips are prepared and are fixed either with a liquid adhesive or a non-liquid adhesive ("solid adhesive at 20° C.") under a 96-well bottomless microplate. Between 7 and 9 wells then have a hydrogel bottom. The central well is filled with coloured water, and the sealing is characterised by the diffusion of coloured water to neighbouring wells.

Production of Polyacrylamide Hydrogels

A. Silanisation of the Base Coverslip for Covalent Grafting of the Polyacrylamide Hydrogel A base glass coverslip, with a diameter of 30 mm, is cleaned in a solution of 0.1 mol/L of sodium hydroxide for 10 min. It is thereafter rinsed thoroughly with water, then with ethanol, and air dried. 500 µl of a silane solution comprising 56 µl of Bind-Silane (GE Healthcare), 484 µl of 10% acetic acid, and 14.46 mL of ultra-pure ethanol are deposited on the coverslip and rubbed with a polyester knit fabric wiper until all traces of solution disappear. A glass coverslip is thus obtained that has aldehyde functional groups at its surface, which will enable the covalent grafting of the polyacrylamide gel.

B. Preparation of a Non-Adhesion Slide

The polymerisation of the hydrogel occurs between the silanised coverslip and a non-adhesion slide which ensures the flatness of the surface of the hydrogel. An optical microscopy slide (26 mm×76 mm) is washed in a solution of oxygenated water/concentrated sulfuric acid in proportions of 1:2, for 10 minutes. The slide is rendered non-adhesive by hydrophobic treatment with Optool (Daikin DSX): immersion for 1 minute in an Optool solution diluted to 1/1000 in perfluorohexane. Then the slide is left for 1 hour in water vapour at 80° C. Finally, it is immersed under slow agitation for 10 minutes in perfluorohexane.

C. Preparation of the Hydrogel (Step a) of the Method)

Composition:

10% acrylamide (250 µl of solution initially at 40%)
  0.5% N,N'-methylenebisacrylamide (Bis) (250 µl of solution initially at 2%)
  0.2% Irgacure 819 w/v (Ciba, photo-initiator)
  1% propylamine (initiator)
  deionised water (490 µl).

Irgacure 819 is weighed in a flask that is opaque to UV light. Propylamine is added to the latter, the entirety of which is then heated at 50° C. for 2 minutes. After heating, a homogeneous, transparent solution is obtained. Water, acrylamide, and bis acrylamide are added quickly therein. Using a pipette, the entire mixture is gently homogenised in order to limit the incorporation of oxygen. 30 µL are deposited on the 30 mm glass coverslip treated according to the above protocol. The coverslip is placed on a sample holder having spacers which maintain a spacing of 40 µm between the coverslip and the non-adhesion slide, deposited on the spacers. The whole unit (slide, solution, coverslip) is illuminated by using a fibre lamp Eleco UVP281 (2 W/cm²) for 7 s. This unit is then immersed in water in order to detach the mask from the hydrogel using forceps. The hydrogel is rinsed 3 times with deionised water and left to swell for 1 night in deionised water. It is then dehydrated at ambient temperature under a laminar flow hood for 4 hours.

Adhering of the Hydrogels Under a 96-Well Microplate

Three liquid adhesives (invention) and a double-sided adhesive tape (comparative) are tested:

Norland NAO 68 (viscosity 5000 mPa·s)
  Norland NOA 81 (viscosity 300 mPa·s)

Loctite S15398 (viscosity 20,000 mPa·s)
  Double-sided tape Tesa® 64621 (90 µm thickness, solvent-free, synthetic rubber on polypropylene support).

The lower surface of a bottomless microwell plate (Greiner Bio One, ref 655000-06) is cleaned with 96% ethanol and air dried.

A. Fixing of the Hydrogel with a Liquid Adhesive (According to the Invention)

An adhesive grid is drawn on the lower surface of the microplate between the wells (step b) of the method). The adhesive line is continuous, which consequently ensures that each tile of the grid represents a continuous zone around a well of the bottomless multi-well plate.

The dehydrated hydrogel fixed on the glass coverslip is placed on the adhered zone (step c) of the method).

Loctite S15398: the coverslip is lightly pressed against the microplate. The adhesive is left to dry for 36 hours (step d')).

NOA 68 and NOA 81: after 5 min, a visual examination shows that the adhesives are in continuous contact with the hydrogel along the gridlines drawn. The adhesives are polymerised by UV lighting: fibre lamp Eleco UVP281 (2 W/cm²) for 5 min (step d) of the method).

The samples are left to rest for 36 hours.

B. Fixing of the Hydrogel with the Adhesive Tape (Comparative)

The adhesive is adhered to the lower surface of the microplate. The wells are cut with a scalpel. The protective film of the adhesive is removed and the dehydrated hydrogel fixed on to the glass coverslip is brought into contact with the adhesive. The coverslip is mechanically hand pressed onto the microplate. The sample is left to rest for 36 hours.

Test of Sealing

Coloured water is prepared by dissolving a spatula tip of the dye Allura Red AC (Disodium 6-hydroxy-5-[(2-methoxy-5-methyl-4-sulfophenyl)azo]-2-naphthalenesulfonate, 496.42 g/mol) (Sigma, ref 458848) in water. This is followed by depositing 200 µL thereof in the central well for each of the conditions. The whole assembly is stored at 4° C. in a dark environment. After 72 hours, the neighbouring wells are observed visually. Then the liquid is withdrawn and the microplate is observed on its lower surface.

This observation is followed by 200 µL again being placed in the central well and the microplate then being kept sealed with parafilm for 10 days. A new visual analysis is thereafter performed.

Results

The 3 liquid adhesives offer identical results. After a period of 72 hours, the wells adjacent to the hydrated well are dry to the eye, that is to say, they do not show any trace of dye and have a refractive index that is visually analogous to that of the dehydrated hydrogel. On the lower surface of the plate, it is observed that the diffusion of the coloured liquid extends up to the first adhesive barrier but not beyond. This result is maintained after 10 days of storage.

On the other hand, the wells of the plate obtained by adhesion with double-sided adhesive tape leak: After a period of 72 hours, 2 wells adjacent to the central well are immersed in the liquid. On the lower face, it is observed that the hydrogel in its entirety has taken on the colour of the dye. After a period of 10 days, the central well is empty, the colouration of the entire hydrogel is more marked, the liquid has leaked from the edges of the plate, extending more than one centimetre from the edges of the central well.

Example 3: Impact on the Sealing of Partial or Total Penetration of the Adhesive Within the Continuous Hydrogel Layer The hydrogel is prepared according to the protocol in Example 2 with the adhesive Norland NOA68 with the following modifications:

glass coverslip with dimensions of 113×75 mm, #1.5 (Live Cell Instrument Co., Ltd, Korea)

non-adhesion slide prepared from a borosilicate slide with dimensions of 100 mm (+/−1.0)×110 mm (+/−1.0) and thickness of 5 mm (+/−0.2) (Pràzisions Glas & Optik GmbH, Germany)

300 µL of the solution of monomers are deposited on the silanised coverslip the solution is polymerised for 8 s under an open Kloe UV KUB 1 lamp equipped with a grating (365 nm, 16 mW/cm$^2$).

The lower surface of a bottomless microwell plate (Greiner Bio One, ref 655000-06) is cleaned with 96% ethanol and air dried. A grid is drawn with the adhesive Norland NOA 68 on the lower surface of the microwell plate between the wells. The adhesive line is continuous. The dehydrated hydrogel fixed on the glass coverslip is placed on the adhered zone. The assembly is left to rest for 5 min, the period of time necessary to observe a change in the refractive index through the glass coverslip along the grid lines (the contact becomes transparent). The whole assembly is then illuminated for 5 min at 365 nm (Kloe, 16 mW/cm$^2$). The assembly is left to rest overnight at ambient temperature. The wells are then hydrated with 200 µl of deionised water for 24 hours. At the end of this period of 24 hours, no leak is detected visually.

The microwell plate is then placed on a dry bath at 37° C. under a laminar flow hood for 24 hours in order for the hydrogel to undergo a step of dehydration. The support gets detached in places, visible by a variation in the refractive index on the lower surface of the microplate (loss of transparency of the coverslip/microplate contact).

The same protocol carried out with a thicker line of adhesive which allowed the adhesive to pass right through the hydrogel and reach the coverslip does not lead to detachment of the support: the tight sealing is effectively maintained even after dehydration of the hydrogel.

Example 4: Impact on the Sealing of Insufficient Activation of the Adhesive

The microwell plate is produced as in Example 2, with the following modification:

The crosslinking of the adhesive NOA 68 is brought about by means of illumination for 1 min at 365 nm (Kloe, 16 mW/cm$^2$).

The wells are then hydrated with 200 µL of deionised water for 3 days and the upper face of the microwell plate is sealed with its cover by means of a grafting tape Parafilm M (Brand). At the end of this period of 3 days, the wells are empty. Water has leaked from the edges of the gel.

This leak disappears with insolation of 5 min instead of 1 min.

Example 5: Test of Toxicity of the Adhesives

Procedure

A drop of adhesive with a diameter of 3 mm is placed at the bottom of a 35 mm diameter, tissue culture-treated Petri dish (Easy Grip Dish, Corning). It is crosslinked according to the manufacturers protocol, then the dish is rinsed with deionised water.

The LN229 cells (ATCC® CRL-2611) are seeded at a density of 5000 cells per cm$^2$ and cultured in DMEM GlutaMax (Gibco, ThermoFisher Scientific reference 31966047) supplemented with 10% FBS (Gibco, ThermoFisher Scientific reference 10270106). The adhesion and survival of the cells as well as the presence of possible contamination are evaluated after 4½ hours and 24 hours of seeding.

Results Based on the Nature of the Adhesive

SuperCyano Adhesive (Loctite): after 4½ hours, the seeded cells do not adhere to the support, unlike the control dish which did not receive any adhesive. In the control dish, the cells already exhibit adhering and spreading.

SuperGlue 3 Adhesive (Jelt): after 4½ hours, the seeded cells do not adhere to the support, unlike the control dish which did not receive any adhesive. In the control dish, the cells already exhibit adhering and spreading. Furthermore, the adhesive releases a "white veil" in the culture medium.

After 24 hours, all the cells seeded with SuperCyano and SuperGlue3 adhesives are dead (cells in suspension), unlike the control dish where they reach confluence.

NOA68 adhesive: after 4½ hours, the cells exhibit adhering and spreading in a manner analogous to the control. After 24 hours, the cells in the control dish and in the dish having a drop of crosslinked NOA68 develop in a similar manner (spreading, proliferation).

None of the conditions present any contamination (turns red in the event of fungal infection, yellow in the event of bacterial contamination).

The invention claimed is:

1. A multi-well plate comprising a support, an upper surface of said support being at least partially covered with a continuous layer of a hydrogel which has a stiffness of from 0.05 kPa to 100 kPa, as measured by atomic force microscopy, said continuous layer of the hydrogel being in contact with a lower surface of a bottomless multi-well plate, wherein said support, said continuous layer of the hydrogel, and the said bottomless multi-well plate are adhered by an adhesive which extends from at least certain portions of the lower surface of the bottomless multi-well plate up to certain portions of the upper surface of said support by passing through the continuous layer of hydrogel, said continuous layer of the hydrogel being partitioned into compartments by means of the adhesive, a bottom of each well of the multi-well plate being entirely surrounded by said at least certain portions of the lower surface of the bottomless multi-well plate.

2. The multi-well plate according to claim 1, wherein the hydrogel comprises a polymer matrix comprising a polymer selected from the group consisting of:

polyacrylamides;

polyethylene glycols, polypropylene glycols and ethylene glycol or propylene glycol copolymers, these latter optionally comprising units resulting from the polymerisation of (meth)acrylate compounds;

polysaccharides, optionally comprising repeating units resulting from the polymerisation of (meth)acrylate compounds;

(co)polymers resulting from the polymerisation of diacrylate and/or (meth)acrylate compounds;

polyvinyl alcohols comprising repeating units resulting from the polymerisation of (meth)acrylate compounds;

dextrans comprising repeating units resulting from the polymerisation of (meth)acrylate compounds;

polypropylene fumarates and poly(propylene fumarate-co-ethylene glycol); and combinations thereof.

3. The multi-well plate according to claim 2, wherein the polymer matrix comprises a polyacrylamide.

4. The multi-well plate according to claim 1, wherein within the same given well, the variability in the stiffness of the hydrogel at the micrometer scale is less than 10%.

5. The multi-well plate according to claim 4, wherein within the same given well, the variability in the stiffness of the hydrogel at the micrometer scale is less than 5%.

6. The multi-well plate according to claim 1, wherein, within the same given well, the hydrogel comprises at least two contiguous zones of distinct stiffness exhibiting a stiffness gradient greater than or equal to 0.05 kPa/µm.

7. The multi-well plate according to claim 1, wherein the surface of the hydrogel of at least one of the wells is functionalised with a polysaccharide and/or a protein and/or a peptide.

8. The multi-well plate according to claim 7, wherein the surface of the hydrogel of at least one of the wells is functionalised with a protein and/or a peptide able to induce cell adhesion via integrins.

9. The multi-well plate according to claim 8, wherein the surface of the hydrogel of at least one of the wells is functionalised with fibronectin, fibrinogen, collagen, laminin, vitronectin or an RGD peptide.

10. The multi-well plate according to claim 7, wherein the surface of the hydrogel of each well is functionalised with a polysaccharide and/or a protein and/or a peptide.

11. A cell culture method in which the multi-well plate according to claim 1 is seeded with cells, and the cells are then cultured.

12. The cell culture method according to claim 11, wherein the cells are stem cells and wherein the stem cells are cultured and differentiated.

13. A plate preparation method for preparing the multi-well plate according to claim 1, said method comprising:

a) providing a substrate comprising said continuous layer of the hydrogel which has a stiffness of from 0.05 kPa to 100 kPa, as measured by atomic force microscopy, said continuous layer at least partially covering the upper surface of the support;

b) applying the adhesive at 20° C., the adhesive being in liquid form at 20° C., over said at least certain portions of the lower surface of a bottomless multi-well plate, the bottom of each well of the multi-well plate being entirely surrounded by the at least certain portions of the lower surface of the bottomless multi-well plate; and c) assembling the substrate and the bottomless multi-well plate by bringing into contact the surface of the hydrogel of the substrate with the lower surface of the bottomless multi-well plate that is at least partially covered with the adhesive, whereby the adhesive at least partially penetrates within the continuous layer of the hydrogel so that said continuous layer of the hydrogel is partitioned into compartments by means of the adhesive.

14. The method according to claim 13, wherein during c), the liquid adhesive penetrates totally within the continuous layer of hydrogel and passes through it until it reaches certain portions of the upper surface of the support.

15. The method according to claim 13, wherein:

between a) and c), said method further comprises an element a1) wherein a polysaccharide and/or a protein and/or a peptide is applied onto at least a portion of the surface of the hydrogel of the substrate; or after c), said method further comprises an element d) wherein a polysaccharide and/or a protein and/or a peptide is applied onto the surface of the hydrogel of at least one well.

16. A screening method for screening of therapeutic molecules, which includes: deposition in the wells of the multi-well plate according to claim 1 of a ligand; bringing into contact of the molecules to be tested with the said ligand; followed thereafter by the identification of the molecules to be tested which have bound themselves to the said ligand.

* * * * *